US012169190B1

(12) United States Patent  
Xu et al.

(10) Patent No.: US 12,169,190 B1  
(45) Date of Patent: Dec. 17, 2024

(54) NON-DESTRUCTIVE FRUIT DEFECT DETECTION METHOD AND SYSTEM BASED ON NEURAL NETWORKS

(71) Applicant: INSTITUTE OF FACILITY AGRICULTURE, GUANGDONG ACADEMY OF AGRICULTURAL SCIENCES, Guangzhou (CN)

(72) Inventors: Sai Xu, Guangzhou (CN); Huazhong Lu, Guangzhou (CN); Xin Liang, Guangzhou (CN)

(73) Assignee: INSTITUTE OF FACILITY AGRICULTURE, GUANGDONG ACADEMY OF AGRICULTURAL SCIENCES, Guangzhou (CN)

(*) Notice: Subject to any disclaimer, the term of this patent is extended or adjusted under 35 U.S.C. 154(b) by 0 days.

(21) Appl. No.: 18/764,238

(22) Filed: Jul. 4, 2024

(30) Foreign Application Priority Data

Oct. 7, 2023 (CN) .......................... 202311282855.3

(51) Int. Cl.
 *G06K 9/00* (2022.01)
 *A01G 25/16* (2006.01)
 (Continued)

(52) U.S. Cl.
 CPC ......... *G01N 33/025* (2013.01); *A01G 25/167* (2013.01); *G06V 10/751* (2022.01); *G06V 20/68* (2022.01)

(58) Field of Classification Search
 CPC ........... G06K 9/00; G06V 10/82; A01D 45/00
 (Continued)

(56) References Cited

U.S. PATENT DOCUMENTS 10,779,472 B2 * 9/2020 Robertson ......... G06F 18/24323  
11,596,104 B2 * 3/2023 Zhang ................... A01D 46/30  
(Continued)

OTHER PUBLICATIONS

Consumers' visual attention to fruit defects and disorders: A case study with apple images Sara R. Jaegera, Lucia Antunezb, Gaston Aresb,c, Jason W. Johnstona, Miriam Halla, F. Roger Harker•* (Year: 2016).*

(Continued)

*Primary Examiner* — Seyed H Azarian  
(74) *Attorney, Agent, or Firm* — Hemisphere Law, PLLC; Zhigang Ma (57) ABSTRACT

A non-destructive fruit defect detection method and system based on neural networks are used to solve problem of inaccurate selection of high-quality fruits by current consumers. The system includes a standard formulation module configured to formulate monitoring standards for different batches and varieties of the fruits to obtain standard detection parameters for the different batches and varieties of the fruits, a preliminary identification module configured to preliminarily identify external conditions of the different batches and varieties of the fruits, a non-destructive detection module configured to non-destructively detect the different batches and varieties of the fruits, generate a fruit abnormal signal or obtain growth deviation values of the different batches and varieties of the fruits, and a quality judgment module configured to judge quality of the different batches and varieties of the fruits. Accurate non-destructive detection for the different batches and varieties of the fruits are realized.

3 Claims, 2 Drawing Sheets

(51) Int. Cl.
    *G01N 33/02*    (2006.01)
    *G06V 10/75*    (2022.01)
    *G06V 10/82*    (2022.01)
    *G06V 20/68*    (2022.01)

(58) Field of Classification Search
    USPC ....... 382/100, 103, 106–107, 109, 123, 141,
                  382/153–156, 162, 172–173, 181, 199,
                  382/224, 219, 254, 286–291, 305, 321;
                              706/14; 356/326, 21
    See application file for complete search history.

(56) References Cited

U.S. PATENT DOCUMENTS

| | | | |
|---|---|---|---|
| 12,096,733 B2 * | 9/2024 | Robertson | G06V 20/10 |
| 2021/0212257 A1 * | 7/2021 | Zhang | A01D 45/00 |
| 2023/0143130 A1 * | 5/2023 | Bhole | G06T 7/0004 |
| | | | 356/326 |
| 2023/0153657 A1 * | 5/2023 | Sagi-Dolev | G06F 18/217 |
| | | | 706/14 |
| 2024/0215488 A1 * | 7/2024 | Taflia | A01D 46/005 |

OTHER PUBLICATIONS

CNIPA, Notification of First Office Action for CN202311282855.3, Feb. 1, 2024.
Institute of Facility Agriculture, Guangdong Academy of Agricultural Sciences (Applicant), Claims of CN202311282855.3 (allowed), Apr. 22, 2024.
CNIPA, Notification to grant patent right for invention in CN202311282855.3, Apr. 28, 2024.

\* cited by examiner

NON-DESTRUCTIVE FRUIT DEFECT DETECTION METHOD AND SYSTEM BASED ON NEURAL NETWORKS

CROSS-REFERENCE TO RELATED APPLICATION

This application claims priority to Chinese Patent Application No. 202311282855.3, filed Oct. 7, 2023, which is herein incorporated by reference in its entirety.

TECHNICAL FIELD

The disclosure relates to the field of fruit detection technologies, and more particularly to a non-destructive fruit defect detection method and system based on neural networks.

BACKGROUND

Fruits refer to edible plant products which are juicy and primarily have a sweet and sour taste. The fruits not only contain abundant vitamin nutrients, but also promote digestion. With the development of planting industry and greenhouse technologies, numerous varieties of the fruits enter the consumer market. While preparing for market consumption, the fruits also need to undergo quality testing.

When consumers purchase a certain variety of the fruits in supermarkets, fruit shops and other places, they usually choose high-quality fruits based on purchasing experience, fruit skins, and other factors. Moreover, different varieties of fruits with a same category and subject can easily mix together to deceive consumers.

Therefore, the disclosure proposes a non-destructive fruit defect detection method and system based on neural networks.

SUMMARY

In response to shortcomings in the related art, a purpose of the disclosure is to provide a non-destructive fruit defect detection method and system based on neural networks.

The technical problem to be solved by the disclosure is: how to realize accurate non-destructive detection to different batches and varieties of fruits.

The purpose of the disclosure can be achieved through below technical solutions.

The non-destructive fruit defect detection system based on the neural networks includes a user terminal, a storage module, a standard formulation module, a preliminary identification module, a data acquisition module, a non-destructive detection module, a quality judgment module and a server.

The storage module is a memory. The standard formulation module is embodied by software stored in at least one memory and executable by at least one processor. The preliminary identification module is embodied by software stored in at least one memory and executable by at least one processor. The data acquisition module is embodied by software stored in at least one memory and executable by at least one processor. The non-destructive detection module is embodied by software stored in at least one memory and executable by at least one processor. The quality judgment module is embodied by software stored in at least one memory and executable by at least one processor.

When selling fruits, an identification code is attached on each fruit. The user terminal is configured to input the identification code of each fruit, take a real-time photo of each fruit with the identification code and send the real-time photo of each fruit with the identification code to the server. The server is configured to send the identification code of each fruit to the storage module and send the real-time photo of each fruit to the preliminary identification module. The storage module is configured to send, based on the identification code of each fruit, standard characteristic data of each fruit to the standard formulation module, standard growth data of each fruit to the non-destructive detection module and a standard fruit photo of each fruit to the preliminary identification module.

The standard formulation module is configured to formulate monitoring standards for different batches and varieties of the fruits to obtain standard detection parameters for the different batches and varieties of the fruits, and send the standard detection parameters to the non-destructive detection module by the server, the preliminary identification module is configured to preliminarily identify external conditions of the different batches and varieties of the fruits to obtain a non-destructive detection signal or a fruit abnormal signal, and send the non-destructive detection signal or the fruit abnormal signal to the server, the server is configured to send the fruit abnormal signal to the user terminal in response to the fruit abnormal signal, and send the non-destructive detection signal to the data acquisition module in response to the non-destructive detection signal.

Before picking the fruits, the data acquisition module is configured to acquire real-time growth data and real-time characteristic data of the different batches and varieties of the fruits based on the non-destructive detection signal, and send the real-time growth data and the real-time characteristic data to the non-destructive detection module by the server, the non-destructive detection module is configured to non-destructively detect the different batches and varieties of the fruits to obtain a fruit abnormal signal or growth deviation values of the different batches and varieties of the fruits.

The quality judgment module is configured to judge quality of the different batches and varieties of the fruits to obtain quality grades of the different batches and varieties of the fruits and send the quality grades to the user terminal by the server, and the user terminal is configured to obtain quality situations of the different batches and varieties of the fruits based on the quality grades.

In an embodiment, the standard characteristic data includes standard fruit weight values, standard fruit length values, standard fruit width values, and standard fruit height values of the different varieties of the fruits.

In an embodiment, the standard growth data includes standard environmental temperatures, standard environmental humidity, standard soil humidity, standard soil potential of hydrogen (pH), and standard light duration of the different varieties of the fruits.

In an embodiment, each identification code includes a name, an origin place and a batch number of the corresponding fruit.

In an embodiment, the real-time growth data includes daily environmental temperatures, daily environmental humidity, daily soil humidity, daily soil pH, and daily light duration of the different batches and varieties of the fruits in a last month before picking the fruits.

In an embodiment, the real-time characteristic data includes daily weight values, daily length values, daily width values and daily height values of the different batches and varieties of the fruits when picking the fruits.

In an embodiment, a formulation process of the standard formulation module comprises following steps.

Corresponding batches and corresponding varieties of the fruits are selected based on the standard characteristic data, and the fruits with same batches and same varieties are classified into fruit samples.

Each fruit sample is detected to obtain sample weight values, sample length values, sample width values and sample height values of the fruit samples.

The sample length values of the fruit samples are iterated and compared to determine a sample weight upper limit value and a sample weight lower limit value of the fruit sample, and the sample weight upper limit value and the sample weight lower limit value together form a weight interval for the fruit samples.

A length interval, a width interval and a height interval of the fruit samples are obtained according to the above step.

The weight interval, the length interval, the width interval and the height interval are the standard detection parameters of the fruits with same batch and variety as the fruit samples.

The standard detection parameters of the different batches and varieties of the fruits are obtained according to the above steps.

In an embodiment, a preliminary identification process of the preliminary identification module includes following steps.

Real-time photos of the different batches and varieties of the fruits are obtained, and standard fruit photos of the fruits are obtained.

The real-time fruit photo of each fruit is compared with the standard fruit photo of each fruit.

The non-destructive detection signal is generated when comparing successfully.

The fruit abnormal signal is generated when comparing unsuccessfully.

In an embodiment, a working process of the non-destructive detection module comprises following steps.

The daily weight values, the daily length values, the daily width values and the daily height values of the different batches and varieties of the fruits are obtained when picking the fruits, the standard detection parameters of the different batches and varieties of the fruits are obtained, and the weight intervals, the length intervals, the width intervals and the height intervals of the different batches and varieties of the fruits are obtained.

Next steps are performed when the daily weight value of the fruit is in the weight interval corresponding to the fruit, the daily length value of the fruit is in the length interval corresponding to the fruit, the daily width value of the fruit is in the width interval corresponding to the fruit and the daily height value of the fruit is in the height interval corresponding to the fruit.

The fruit abnormal signal is generated when any one of below conditions occurs: the daily weight value of the fruit is not in the weight interval corresponding to the fruit, the daily length value of the fruit is not in the length interval corresponding to the fruit, the daily width value of the fruit is not in the width interval corresponding to the fruit and the daily height value of the fruit is not in the height interval corresponding to the fruit.

In an embodiment, the working process of the non-destructive detection module further includes the next steps.

The daily environmental temperatures, the daily environmental humidity, the daily soil humidity, the daily soil pH, and the daily light duration of the different batches and varieties of the fruits in the last month before picking the fruits are obtained.

The daily environmental temperatures are added together of each batch of the fruits to obtain a real-time environmental temperature of each batch and each variety of the fruits.

Real-time environmental temperature humidity, real-time soil humidity, real-time soil pH and real-time light duration of each batch and each variety of the fruits are obtained accordingly.

The standard growth data including the standard environmental temperature, the standard environmental humidity, the standard soil humidity, the standard soil pH, and the standard light duration of each batch and each variety of the fruits is obtained.

A deviation value between the real-time environmental temperature and the standard environmental temperature of each batch and each variety of the fruits is calculated.

A humidity deviation value, a soil humidity deviation value, a soil pH deviation value and a light duration deviation value of each batch and each variety of the fruits are calculated accordingly.

The growth deviation value of each batch and each variety of the fruits is calculated.

In an embodiment, the non-destructive detection module is configured to send the fruit abnormal signal or the growth deviation value of each batch and each variety of the fruits to the server.

The server is configured to send the fruit abnormal signal to the user terminal in response to the fruit abnormal signal, the user terminal is configured to check the quality situations of the fruits after receiving the fruit abnormal signal.

The server is configured to send the growth deviation value of each batch and each variety of the fruits to the quality judgment module in response to the growth deviation value of each batch and each variety of the fruits.

In an embodiment, a judgment process of the quality judgment module includes following steps.

The growth deviation value of each batch and each variety of the fruits is obtained.

The growth deviation value is compared to growth deviation thresholds to judge the quality grade of a corresponding batch and variety of the fruits as excellent, average or inferior.

To achieve the purpose of the disclosure, the disclosure further provides the non-destructive fruit defect detection method based on the neural networks, including following steps.

S100, the user terminal inputs the identification code and the real-time photo of each fruit with the identification code.

S200, the standard formulation module formulates the monitoring standards for the different batches and varieties of the fruits to obtain the standard detection parameters for the different batches and varieties of the fruits, and the standard detection parameters are sent to the non-destructive detection module.

S300, the preliminary identification module preliminarily identifies the external conditions of the different batches and varieties of the fruits and generates the non-destructive detection signal or the fruit abnormal signal, and the non-destructive detection signal is sent to the data acquisition module when generating the non-destructive detection signal.

S400, the data acquisition module acquires the real-time growth data and the real-time characteristic data of the different batches and varieties of the fruits, and the real-time growth data and the real-time characteristic data are sent to the non-destructive detection module.

S500, the non-destructive detection module non-destructively detects the different batches and varieties of the fruits, generates the fruit abnormal signal, or obtains and sends the growth deviation values of the different batches and varieties of the fruits to the quality judgment module.

S600, the quality judgment module judges the quality of the different batches and varieties of the fruits and determines the quality grades of the different batches and varieties of the fruits.

The disclosure has following beneficial effects compared to the related art.

The disclosure first uses the standard formulation module to formulate the monitoring standards for the different batches and varieties of the fruits to obtain the standard detection parameters for the different batches and varieties of the fruits, and update and improve the standard detection parameters in real-time based on network and other related factors. During actual consumption, a consumer input identification codes and take real-time fruit photos of the fruits, the preliminary identification module is used to preliminarily identify the external conditions of the different batches and varieties of the fruits and generate the non-destructive detection signal or the fruit abnormal signal. Then, the non-destructive detection module is used to non-destructively detect the different batches and varieties of the fruits, generate the fruit abnormal signal or obtain and send growth deviation values of the different batches and varieties of the fruits to the quality judgment module, and the quality judgment module is used to judge the quality of the different batches and varieties of the fruits, and determine and send the quality grades of the different batches and varieties of the fruits to the consumer. The disclosure realizes the accurate non-destructive detection to the different batches and varieties of the fruits.

BRIEF DESCRIPTION OF DRAWINGS

For the convenience of those skilled in the art to understand, the disclosure is further explained in conjunction with the accompanying drawings.

DETAILED DESCRIPTION OF EMBODIMENTS

A clear and complete description of the technical solutions of the disclosure is provided below in conjunction with the embodiments. Apparently, the described embodiments are only a part of the embodiments of the disclosure, not all of them. Based on the embodiments in the disclosure, all other embodiments obtained by those skilled in the art without creative labor fall within the scope of protection of the disclosure.

Figure 1:
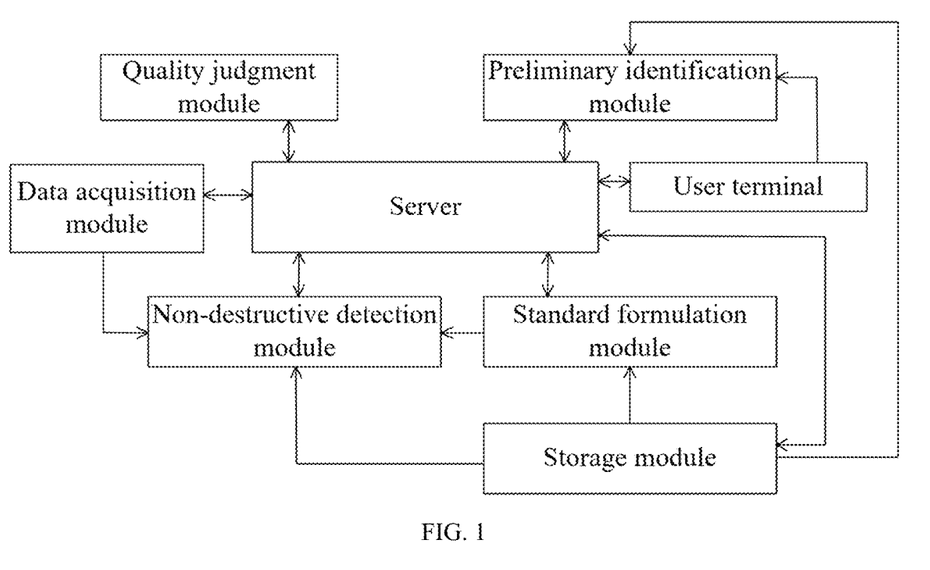
FIG. 1 illustrates an overall system diagram of the disclosure.

In an embodiment, referring to FIG. 1, a non-destructive fruit defect detection system based on neural networks is mainly used for fruit detection when a consumer purchases fruits, thus the consumer can purchase desired and high-quality fruits. The system (i.e., the non-destructive fruit defect detection system) includes a user terminal, a storage module, a standard formulation module, a preliminary identification module, a data acquisition module, a non-destructive detection module, a quality judgment module and a server.

In the embodiment, the user terminal is used for the consumer to input personal information, register and log in to the system, and to send the personal information to the server. The personal information includes the name and phone number of the consumer, etc.

The storage module is configured to save standard characteristic data, standard growth data and standard fruit photos of different varieties of the fruits. The standard characteristic data includes standard fruit weight values, standard fruit length values, standard fruit width values, and standard fruit height values of the different varieties of the fruits. The standard growth data includes standard environmental temperatures, standard environmental humidity, standard soil humidity, standard soil pH, and standard light duration of the different varieties of the fruits.

It should be noted that the standard characteristic data, standard detection data, and the standard growth data can all be obtained from various planting literature and agricultural planting websites.

When selling the fruits, an identification code is attached on each fruit. The identification code includes the fruit's name, place of origin, and batch number. The user terminal is configured to input the identification code of each fruit, take a real-time photo of each fruit with the identification code and send the real-time photo of each fruit with the identification code to the server. The server is configured to send the identification code of each fruit to the storage module and send the real-time photo of each fruit to the preliminary identification module. The storage module is configured to send, based on the corresponding identification code, the standard characteristic data corresponding to the fruit to the standard formulation module, send the standard growth data corresponding to the fruit to the non-destructive detection module and send the standard fruit photo corresponding to the fruit to the preliminary identification module.

In the embodiment, the standard formulation module can combine the standard characteristic data from websites and documents etc., to construct current detection standards for different batches and varieties of the fruits based on the standard characteristic data, achieving deep learning and self-improvement of fruit detection standards.

The standard formulation module is configured to formulate monitoring standards for the different batches and varieties of the fruits, and a formulation process of the standard formulation module includes following steps.

Corresponding batches and corresponding varieties of the fruits are selected based on the standard characteristic data, and the fruits are classified into fruit samples based on the same batches and the same varieties.

Each fruit sample is detected to obtain sample weight values, sample length values, sample width values and sample height values of the fruit samples.

The sample length values of the fruit samples are iterated and compared to determine a sample weight upper limit value and a sample weight lower limit value of the fruit samples, and the sample weight upper limit value and the sample weight lower limit value together form a weight interval for the fruit samples.

A length interval, a width interval and a height interval of the fruit samples are obtained according to the above step.

The weight interval, the length interval, the width interval and the height interval are the standard detection parameters of the fruits with same batch and variety as the fruit samples.

The standard detection parameters of the different batches and varieties of the fruits are obtained according to the above steps. The standard detection parameters can be regarded as an algorithm mathematical model.

The standard formulation module is configured to send the standard detection parameters for the different batches and varieties of the fruits to the server, and the server is configured to send the standard detection parameters for the different batches and varieties of the fruits to the non-destructive detection module.

The preliminary identification module is configured to preliminarily identify external conditions of the different batches and varieties of the fruits, and a preliminary identification process of the preliminary identification module includes following steps.

Real-time photos of the different batches and varieties of the fruits are obtained, and standard fruit photos of the fruits are obtained The real-time fruit photo of each fruit is compared with the standard fruit photo of each fruit.

Specifically, the method for comparing photos is based on the related art, which can be obtained by using image similarity comparison algorithms. The image similarity comparison algorithms include pixel comparison, centroid comparison, projection comparison, and block comparison. Meanwhile, the image comparison can also be carried out through hash algorithms, including average hash algorithm, difference hash algorithm and perceptual hash algorithm, etc.

For example, the average hash algorithm: 1, an image is scaled to 8×8, the structure is preserved while discarding details; 2, the scaled image is converted to a grayscale image; 3, average value calculation: an average value of all pixels of the grayscale image is calculated; 4, comparison: when a pixel is greater than 1, the pixel is denoted as 1, otherwise denoted as 0, resulting in a total of 64 bits; 5, hash generation: 1 and 0 generated in the above step are combined sequentially to obtain a hash of the image; 6, hash comparison: hashes of two images are compared, the Hamming distance is calculated, i.e., the number of bits that differ between the two 64-bit hash values. The fewer the number of differing bits, the more similar the images are.

The non-destructive detection signal is generated when comparing successfully (i.e., an image similarity reaches a target similarity). A fruit abnormal signal is generated when comparing unsuccessfully (i.e., the image similarity does not reach the target similarity).

The preliminary identification module is configured to send the non-destructive detection signal or the fruit abnormal signal to the server. The server is configured to send the fruit abnormal signal to the user terminal in response to the fruit abnormal signal, and send the non-destructive detection signal to the data acquisition module in response to the non-destructive detection signal.

Before picking the fruits, the data acquisition module is configured to acquire real-time growth data and real-time characteristic data of the different batches and varieties of the fruits based on the non-destructive detection signal and send the real-time growth data and the real-time characteristic data to the server. The server is configured to send the real-time growth data and the real-time characteristic data to the non-destructive detection module.

It should be noted that the real-time growth data includes daily environmental temperatures, daily environmental humidity, daily soil humidity, daily soil pH, and daily light duration for the different batches and varieties of the fruits in a last month before picking the fruits. The real-time characteristic data includes daily weight values, daily length values, daily width values and daily height values of the different batches and varieties of the fruits when picking the fruits.

The non-destructive detection module is configured to non-destructively detect the different batches and varieties of the fruits, and a working process of the non-destructive detection module includes following steps.

The daily weight values, the daily length values, the daily width values and the daily height values of the different batches and varieties of the fruits are obtained when picking the fruits, the standard detection parameters of the different batches and varieties of the fruits are obtained, and the weight intervals, the length intervals, the width intervals and the height intervals of the different batches and varieties of the fruits are obtained.

Next steps are performed when the daily weight value of the fruit is in the weight interval corresponding to the fruit, the daily length value of the fruit is in the length interval corresponding to the fruit, the daily width value of the fruit is in the width interval corresponding to the fruit and the daily height value of the fruit is in the height interval corresponding to the fruit.

A fruit abnormal signal is generated when any one of below conditions occurs: the daily weight value of the fruit is not in the weight interval corresponding to the fruit, the daily length value of the fruit is not in the length interval corresponding to the fruit, the daily width value of the fruit is not in the width interval corresponding to the fruit and the daily height value of the fruit is not in the height interval corresponding to the fruit.

The daily environmental temperatures, the daily environmental humidity, the daily soil humidity, the daily soil pH, and the daily light duration of the different batches and varieties of the fruits in the last month before picking the fruits are obtained.

The daily environmental temperatures are added together of each batch of the fruits to obtain a real-time environmental temperature of each batch and each variety of the fruits.

Real-time environmental temperature humidity, real-time soil humidity, real-time soil pH and real-time light duration of each batch and each variety of the fruits are obtained accordingly.

The standard growth data including the standard environmental temperature, the standard environmental humidity, the standard soil humidity, the standard soil pH, and the standard light duration of each batch and each variety of the fruits is obtained.

A deviation value denoted as $WC_{ui}$ between the real-time environmental temperature and the standard environmental temperature of each batch and each variety of the fruits is calculated. u represents a serial number of the fruit, i represents a serial number of the batch corresponding to the fruit, $u=1, 2, \ldots, z$, z is a positive integer, $i=1, 2, \ldots, x$, and x is a positive integer.

A humidity deviation value $SC_{ui}$, a soil humidity deviation value $TSC_{ui}$, a soil pH deviation value $SJ_{ui}$ and a light duration deviation value $GT_{ui}$ of each batch and each variety of the fruits are calculated accordingly.

The growth deviation value $SP_{ui}$ of each batch and each variety of the fruits is calculated through a formula: $SP_{ui}=SC_{ui}\times a1+TSC_{ui}\times a2+SJ_{ui}\times a3+GT_{ui}\times a4$, where a1, a2, a3 and a4 represent weight coefficients which are fixed values, and $a1+a2+a3+a4=1$.

The non-destructive detection module is configured to send the fruit abnormal signal or the growth deviation value of each batch and each variety of the fruits to the server, the server is configured to send the fruit abnormal signal to the user terminal when receiving the fruit abnormal signal, the user terminal is configured to check the quality situations of the fruits after receiving the fruit abnormal signal, the server is configured to send the growth deviation value of each batch and each variety of the fruits to the quality judgment module when receiving the growth deviation value of each batch and each variety of the fruits.

The quality judgment module is configured to judge quality of the different batches and varieties of the fruits, and a judgment process of the quality judgment module includes following steps.

The growth deviation value $SP_{ui}$ of each batch and each variety of the fruits is obtained.

In response to the growth deviation value $SP_{ui}$ being less than X1, the quality grade of the corresponding batch and variety of the fruits is determined as excellent.

In response to the growth deviation value $SP_{ui}$ being less than X2 but not less than X1, the quality grade of the corresponding batch and variety of the fruits is determined as average.

In response to the growth deviation value $SP_{ui}$ being not less than X2, the quality grade of the corresponding batch and variety of the fruits is determined as inferior, X1 and X2 represent growth deviation thresholds and X1 is less than X2.

The quality judgment module is configured to send the quality grade of each batch and each variety of the fruits to the server, the server is configured to send the quality grade of each batch and each variety of the fruits to the user terminal, and the user terminal is configured to obtain the quality condition of each batch and each variety of the fruits based on the quality grade.

In this specification, if there are any corresponding calculation formulas, the calculation formulas are all dimensionless and calculated by their numerical values. The weight coefficients, proportional coefficients, and other coefficients in the formulas are set to quantify the various parameters into a result value. Regarding magnitude of the weight coefficients and proportional coefficients, as long as they do not affect the proportional relationship between the parameters and the result value, it is acceptable.

Figure 2:
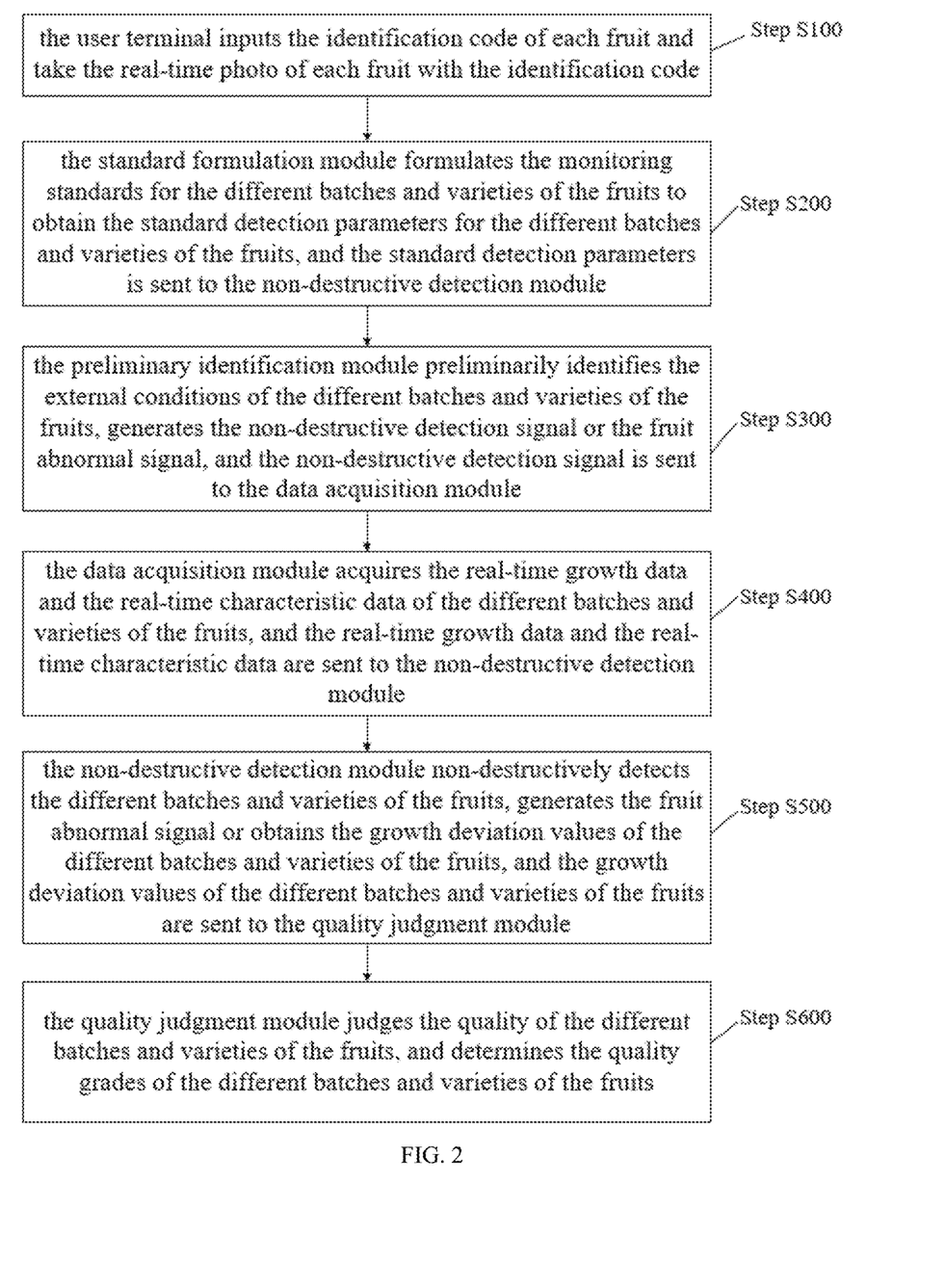
FIG. 2 illustrates a method flowchart of the disclosure.

In another embodiment, referring to FIG. 2, a non-destructive fruit defect detection method based on the neural networks includes following steps.

S100, the user terminal inputs the identification code of each fruit and take the real-time photo of each fruit with the identification code, sends the identification code and the real-time photo of each fruit to the server. The server sends the identification code to the storage module, and sends the real-time photo to the preliminary identification module. The storage module sends the standard characteristic data corresponding the fruits based on the identification code to the standard formulation module, sends the standard growth data based on the identification code to the non-destructive detection module and sends the standard fruit photo of each fruit based on the identification code to the preliminary identification module.

S200, the standard formulation module formulates the monitoring standards for the different batches and varieties of the fruits to obtain the standard detection parameters for the different batches and varieties of the fruits, and the standard detection parameters are sent to the non-destructive detection module.

In this embodiment, a formulation process in the step S200 specifically includes following steps.

S201, the corresponding batches and corresponding varieties of the fruits are selected based on the standard characteristic data, and the fruits with same batches and same varieties are classified into the fruit samples. Each fruit sample is detected to obtain sample weight values, sample length values, sample width values and sample height values of the fruit samples.

S202, the sample length values of the fruit samples are iterated and compared to determine the sample weight upper limit value and the sample weight lower limit value of the fruit samples, and the sample weight upper limit value and the sample weight lower limit value together form the weight interval for the fruit samples. The length interval, the width interval and the height interval of the fruit samples are obtained accordingly.

S203, the weight interval, the length interval, the width interval and the height interval are the standard detection parameters of fruits with the same batch and variety as the fruit samples. The standard detection parameters of the different batches and varieties of the fruits are obtained accordingly.

S300, the preliminary identification module preliminarily identifies the external conditions of the different batches and varieties of the fruits, obtains the real-time photos of the different batches and varieties of the fruits and the standard fruit photos of the fruits, and compares the real-time fruit photo of each fruit with the standard fruit photo of each fruit. The non-destructive detection signal is generated when comparing successfully, and the fruit abnormal signal is generated when comparing unsuccessfully. The preliminary identification module sends the non-destructive detection signal or the fruit abnormal signal to the server. The server sends the fruit abnormal signal to the user terminal when receiving the fruit abnormal signal, and sends the non-destructive detection signal to the data acquisition module when receiving the non-destructive detection signal.

S400, the data acquisition module acquires the real-time growth data and the real-time characteristic data of the different batches and varieties of the fruits, and sends the real-time growth data and the real-time characteristic data to the server. The server sends the real-time growth data and the real-time characteristic data to the non-destructive detection module.

S500, the non-destructive detection module non-destructively detects the different batches and varieties of the fruits, generates the fruit abnormal signal or obtains the growth deviation values of the different batches and varieties of the fruits, and sends the fruit abnormal signal or the growth deviation values to the server. The server sends the fruit abnormal signal to the user terminal when receiving the fruit abnormal signal, and the user terminal checks the quality situations of the fruits after receiving the fruit abnormal signal. The server sends the growth deviation values of the different batches and varieties of the fruits to the quality judgment module when receiving the growth deviation values of the different batches and varieties of the fruits.

In this embodiment, a non-destructive detection process of the non-destructive detection module in the step S500 specifically includes following steps.

S501, the daily weight values, the daily length values, the daily width values and the daily height values of the different batches and varieties of the fruits are obtained when picking the fruits.

S502, the standard detection parameters of different batches and varieties of the fruits are obtained, and the weight intervals, the length intervals, the width intervals and the height intervals of the different batches and varieties of the fruits are obtained.

S503, the fruit abnormal signal is generated when any one of below conditions occurs: the daily weight value of the fruit is not in the weight interval corresponding to the fruit, the daily length value of the fruit is not in the length interval corresponding to the fruit, the daily width value of the fruit is not in the width interval corresponding to the fruit and the daily height value of the fruit is not in the height interval corresponding to the fruit.

S504, next steps are performed when the daily weight value of the fruit is in the weight interval corresponding to the fruit, the daily length value of the fruit is in the length interval corresponding to the fruit, the daily width value of the fruit is in the width interval corresponding to the fruit and the daily height value of the fruit is in the height interval corresponding to the fruit.

S505, the daily environmental temperatures, the daily environmental humidity, the daily soil humidity, the daily soil pH, and the daily light duration of the different batches and varieties of the fruits in the last month before picking the fruits are obtained.

S506, the daily environmental temperatures are added together for each batch of the fruits to obtain the real-time environmental temperature of each batch and each variety of the fruits. The real-time environmental temperature humidity, the real-time soil humidity, the real-time soil pH and the real-time light duration of each batch and each variety of the fruits are obtained accordingly. The standard growth data including the standard environmental temperature, the standard environmental humidity, the standard soil humidity, the standard soil pH, and the standard light duration of each batch and each variety of the fruits is obtained.

S507, the deviation value between the real-time environmental temperature and the standard environmental temperature of each batch and each variety of the fruits is calculated. The humidity deviation value, the soil humidity deviation value, the soil pH deviation value and the light duration deviation value of each batch and each variety of the fruits are calculated accordingly.

S508, the growth deviation value of each batch and each variety of the fruits is calculated.

S600, the quality judgment module judges the quality of the different batches and varieties of the fruits, obtains the growth deviation values, compares the growth deviation values with the growth deviation thresholds, and determines the quality grades of different batches and varieties of the fruits as excellent, average or inferior. The quality judgment module sends the quality grades of the different batches and varieties of the fruits to the server. The server sends the quality grades of the different batches and varieties of the fruits to the user terminal. The user terminal obtains the quality conditions of the different batches and varieties of the fruits based on the quality grades.

The preferred embodiments listed above in the disclosure are only intended to illustrate the disclosure. The preferred embodiments do not provide a detailed description of all details, and are not be limited to the specific implementation of the disclosure. Apparently, many modifications and changes can be made based on the content of this specification. The specification selects and specifically describes the embodiments in order to better explain the principles and practical applications of the disclosure, in order that those skilled in the art can better understand and utilize the disclosure. The disclosure is limited only by the claims and all their scope and equivalents.

What is claimed is:

1. A non-destructive fruit defect detection system based on neural networks, comprising: a user terminal, a storage module, a standard formulation module, a preliminary identification module, a data acquisition module, a non-destructive detection module, a quality judgment module and a server;

wherein when selling fruits, an identification code is attached on each fruit, the user terminal is configured to input the identification code of each fruit, take a real-time photo of each fruit with the identification code and send the real-time photo of each fruit with the identification code to the server, the server is configured to send the identification code of each fruit to the storage module and send the real-time photo of each fruit to the preliminary identification module, and the storage module is configured to send, based on the identification code of each fruit, standard characteristic data of each fruit to the standard formulation module, standard growth data of each fruit to the non-destructive detection module and a standard fruit photo of each fruit to the preliminary identification module;

wherein the standard formulation module is configured to formulate monitoring standards for different batches and varieties of the fruits to obtain standard detection parameters for the different batches and varieties of the fruits, and send the standard detection parameters to the non-destructive detection module by the server, the preliminary identification module is configured to preliminarily identify external conditions of the different batches and varieties of the fruits to obtain a non-destructive detection signal or a fruit abnormal signal, and send the non-destructive detection signal or the fruit abnormal signal to the server, the server is configured to send the fruit abnormal signal to the user terminal in response to the fruit abnormal signal, and send the non-destructive detection signal to the data acquisition module in response to the non-destructive detection signal;

wherein before picking the fruits, the data acquisition module is configured to acquire real-time growth data and real-time characteristic data of the different batches and varieties of the fruits based on the non-destructive detection signal, and send the real-time growth data and the real-time characteristic data to the non-destructive detection module by the server, the non-destructive detection module is configured to non-destructively detect the different batches and varieties of the fruits to obtain a fruit abnormal signal or growth deviation values of the different batches and varieties of the fruits;

wherein the quality judgment module is configured to judge quality of the different batches and varieties of the fruits to obtain quality grades of the different batches and varieties of the fruits and send the quality grades to the user terminal by the server, and the user terminal is configured to obtain quality situations of the different batches and varieties of the fruits based on the quality grades;

wherein the standard characteristic data comprises: standard fruit weight values, standard fruit length values, standard fruit width values, and standard fruit height values of the different varieties of the fruits;

wherein the standard growth data comprises: standard environmental temperatures, standard environmental humidity, standard soil humidity, standard soil potential of hydrogen (pH), and standard light duration of the different varieties of the fruits;

wherein each identification code comprises a name, an origin place and a batch number of the corresponding fruit;

wherein the real-time growth data comprises daily environmental temperatures, daily environmental humidity, daily soil humidity, daily soil pH, and daily light duration of the different batches and varieties of the fruits in a last month before picking the fruits;

wherein the real-time characteristic data comprises daily weight values, daily length values, daily width values and daily height values of the different batches and varieties of the fruits when picking the fruits;

wherein a formulation process of the standard formulation module comprises following steps:

selecting corresponding batches and corresponding varieties of the fruits based on the standard characteristic data, and classifying the fruits with same batches and same varieties into fruit samples;

detecting each fruit sample to obtain sample weight values, sample length values, sample width values and sample height values of the fruit samples;

iterating through and comparing the sample length values of the fruit samples to determine a sample weight upper limit value and a sample weight lower limit value of the fruit samples, wherein the sample weight upper limit value and the sample weight lower limit value together form a weight interval for the fruit samples;

obtaining a length interval, a width interval and a height interval of the fruit samples according to the above step, wherein the weight interval, the length interval, the width interval and the height interval are the standard detection parameters of the fruits with same batch and variety as the fruit samples; and obtaining the standard detection parameters of the different batches and varieties of the fruits according to the above steps;

wherein a working process of the non-destructive detection module comprises following steps:

obtaining the daily weight values, the daily length values, the daily width values and the daily height values of the different batches and varieties of the fruits when picking the fruits, obtaining the standard detection parameters of the different batches and varieties of the fruits, and obtaining the weight intervals, the length intervals, the width intervals and the height intervals of the different batches and varieties of the fruits;

performing next steps when the daily weight value of the fruit is in the weight interval corresponding to the fruit, the daily length value of the fruit is in the length interval corresponding to the fruit, the daily width value of the fruit is in the width interval corresponding to the fruit and the daily height value of the fruit is in the height interval corresponding to the fruit; or generating the fruit abnormal signal when any one of below conditions occurs: the daily weight value of the fruit is not in the weight interval corresponding to the fruit, the daily length value of the fruit is not in the length interval corresponding to the fruit, the daily width value of the fruit is not in the width interval corresponding to the fruit and the daily height value of the fruit is not in the height interval corresponding to the fruit;

wherein the working process of the non-destructive detection module further comprises the next steps:

obtaining the daily environmental temperatures, the daily environmental humidity, the daily soil humidity, the daily soil pH, and the daily light duration of the different batches and varieties of the fruits in the last month before picking the fruits;

adding the daily environmental temperatures of each batch of the fruits to obtain a real-time environmental temperature of each batch and each variety of the fruits;

obtaining real-time environmental temperature humidity, real-time soil humidity, real-time soil pH and real-time light duration of each batch and each variety of the fruits accordingly;

obtaining the standard growth data comprising the standard environmental temperature, the standard environmental humidity, the standard soil humidity, the standard soil pH, and the standard light duration of each batch and each variety of the fruits;

calculating a deviation value denoted as $WCui$ between the real-time environmental temperature and the standard environmental temperature of each batch and each variety of the fruits, wherein $WCui$ represents the deviation value between the real-time environmental temperature and the standard environmental temperature of a u-th fruit in an i-th batch, u represents a serial number of the fruit, i represents a serial number of the batch corresponding to the fruit, u=1, 2, . . . , z, z is a positive integer, i=1, 2, . . . , x, and x is a positive integer;

calculating accordingly a humidity deviation value $SCui$, a soil humidity deviation value $TSCui$, a soil pH deviation value $SJui$ and a light duration deviation value $GTui$ of each batch and each variety of the fruits, wherein $SCui$ represents the humidity deviation value of the u-th fruit in the i-th batch, $TSCui$ represents the soil humidity deviation value of the u-th fruit in the i-th batch, $SJui$ represents the soil pH deviation value of the u-th fruit in the i-th batch, and $GTui$ represents the light duration deviation value of the u-th fruit in the i-th batch; and calculating the growth deviation value $SPui$ of each batch and each variety of the fruits through a formula: $SPui = SCui \times a1 + TSCui \times a2 + SJui \times a3 + GTui \times a4$, where $SPui$ represents the growth deviation value of the u-th fruit in the i-th batch, a1, a2, a3 and a4 represent weight coefficients which are fixed values, and a1+a2+a3+a4=1;

wherein the non-destructive detection module is configured to send the fruit abnormal signal or the growth deviation value of each batch and each variety of the fruits to the server, the server is configured to send the fruit abnormal signal to the user terminal in response to the fruit abnormal signal, the user terminal is configured to check the quality situations of the fruits after receiving the fruit abnormal signal, the server is configured to send the growth deviation value of each batch and each variety of the fruits to the quality judgment module in response to the growth deviation value of each batch and each variety of the fruits;

wherein the quality judgment module is configured to judge the quality of the different batches and varieties of the fruits, a judgment process comprises following steps:

obtaining the growth deviation value $SPui$ of each batch and each variety of the fruits;

in response to the growth deviation value $SPui$ being less than X1, determining the quality grade of the corresponding batch and variety of the fruits is excellent;

in response to the growth deviation value $SPui$ being less than X2 but not less than X1, determining the quality grade of the corresponding batch and variety of the fruits is average; and in response to the growth deviation value $SPui$ being not less than X2, determining the quality grade of the corresponding batch and variety of the fruits is inferior;

wherein X1 and X2 represent growth deviation thresholds and X1 is less than X2; and wherein the quality judgment module is configured to send the quality grade of each batch and each variety of the fruits to the server, the server is configured to send the quality grade of each batch and each variety of the fruits to the user terminal, and the user terminal is configured to obtain the quality condition of each batch and each variety of the fruits based on the quality grade.

2. The non-destructive fruit defect detection system based on the neural networks as claimed in claim 1, wherein a preliminary identification process of the preliminary identification module comprises following steps:

obtaining real-time photos of the different batches and varieties of the fruits, and obtaining standard fruit photos of the fruits;

comparing the real-time fruit photo of each fruit with the standard fruit photo of each fruit;

generating the non-destructive detection signal when comparing successfully; or generating the fruit abnormal signal when comparing unsuccessfully.

3. A non-destructive fruit defect detection method based on the neural networks according to the non-destructive fruit defect detection system based on the neural networks as claimed in claim 1, comprising following steps:

S100, inputting, by the user terminal, the identification code and the real-time photo of each fruit with the identification code;

S200, formulating, by the standard formulation module, the monitoring standards for the different batches and of the fruits to obtain the standard detection parameters for the different batches and varieties of the fruits, and sending the standard detection parameters to the non-destructive detection module;

S300, preliminarily identifying, by the preliminary identification module, the external conditions of the different batches and varieties of the fruits, generating, by the preliminary identification module, the non-destructive detection signal or the fruit abnormal signal, and sending the non-destructive detection signal to the data acquisition module when generating the non-destructive detection signal;

S400, acquiring, by the data acquisition module, the real-time growth data and the real-time characteristic data of the different batches and varieties of the fruits, and sending the real-time growth data and the real-time characteristic data to the non-destructive detection module;

S500, non-destructively detecting, by the non-destructive detection module, the different batches and varieties of the fruits, generating, by the non-destructive detection module, the fruit abnormal signal, or obtaining and sending the growth deviation values of the different batches and varieties of the fruits to the quality judgment module; and S600, judging, by the quality judgment module, the quality of the different batches and varieties of the fruits and determining, by the quality judgment module, the quality grades of the different batches and varieties of the fruits.

* * * * *